United States Patent
Qin et al.

(10) Patent No.: US 10,751,445 B2
(45) Date of Patent: Aug. 25, 2020

(54) IRON-BASED ABSORBABLE AND IMPLANTABLE MEDICAL DEVICE AND MANUFACTURING METHOD THEREOF

(71) Applicant: Lifetech Scientific (Shenzhen) Co., Ltd., Shenzhen (CN)

(72) Inventors: Li Qin, Shenzhen (CN); Deyuan Zhang, Shenzhen (CN); Wenjiao Lin, Shenzhen (CN); Haiping Qi, Shenzhen (CN); Ziqiang Liu, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 125 days.

(21) Appl. No.: 15/737,873

(22) PCT Filed: Jun. 1, 2016

(86) PCT No.: PCT/CN2016/084297
§ 371 (c)(1),
(2) Date: Dec. 19, 2017

(87) PCT Pub. No.: WO2017/000736
PCT Pub. Date: Jan. 5, 2017

(65) Prior Publication Data
US 2019/0008994 A1 Jan. 10, 2019

(30) Foreign Application Priority Data
Jul. 1, 2015 (CN) .......................... 2015 1 0377519

(51) Int. Cl.
| | | |
|---|---|---|
| *A61L 27/04* | (2006.01) | |
| *A61L 31/16* | (2006.01) | |
| *A61L 31/14* | (2006.01) | |
| *A61L 31/12* | (2006.01) | |
| *A61L 27/54* | (2006.01) | |
| *A61L 27/58* | (2006.01) | |

(52) U.S. Cl.
CPC ............ *A61L 27/042* (2013.01); *A61L 27/54* (2013.01); *A61L 27/58* (2013.01); *A61L 31/12* (2013.01); *A61L 31/122* (2013.01); *A61L 31/14* (2013.01); *A61L 31/148* (2013.01); *A61L 31/16* (2013.01)

(58) Field of Classification Search
CPC ........ A61L 31/022; A61L 31/10; A61L 31/12; A61L 31/148; A61L 31/16; A61L 31/14; A61L 27/58; A61L 27/54; A61L 27/34; A61L 27/042; A61L 2400/18; A61L 2300/802; A61L 2300/42; A61L 2300/418; A61L 2300/416; A61L 2300/41; A61L 2400/02; A61L 27/3687; A61K 2800/596; A61K 8/463; Y10S 623/918

See application file for complete search history.

(56) References Cited

U.S. PATENT DOCUMENTS

2009/0281613 A1   11/2009   Atanasoska et al.

FOREIGN PATENT DOCUMENTS

| CN | 101292651 | | 10/2008 |
|---|---|---|---|
| CN | 102008751 A | * | 4/2011 |
| CN | 102008751 A | | 4/2011 |
| CN | 102228721 | | 11/2011 |
| CN | 102961787 | | 3/2013 |
| CN | 104587534 | | 5/2015 |
| CN | 104587534 A | * | 5/2015 |
| CN | 104587534 A | | 5/2015 |
| WO | WO-2006060033 A1 | * | 6/2006 ............. A61L 27/58 |

OTHER PUBLICATIONS

CN-102008751-A, Espacenet English Translation, downloaded Jun. 2019 (Year: 2019).*
CN-102008751-A, Espacenet English translation, Downloaded in Sep. 2019 (Year: 2019).*
CN-104587534-A, Espacenet English translation, Downloaded in Sep. 2019 (Year: 2019).*
Kellou-Kerkouche, et al, (Journal of Materials, 2013, vol. 2013, pp. 1-11) (Year: 2013).*
Office Action dated Jan. 8, 2019 for corresponding China Application No. 201510377519.6.
Chen, Feng. "The Application Properties and Structures of Surfactant", Prperties, Structures, Calculation and Applications of Surfactant, Mar. 31, 2004 pp. 184-187.
International Search Report dated Aug. 22, 2016 for PCT/CN2016/084297.

* cited by examiner

*Primary Examiner* — Mark V Stevens
(74) *Attorney, Agent, or Firm* — Raymond Sun

(57) ABSTRACT

Provided are an iron-based absorbable and implantable medical device and manufacturing method thereof. The iron-based absorbable and implantable medical device (1) comprises a substrate (11), a degradable polymer layer (12), and an anionic surfactant layer (13) located between the substrate (11) and the degradable polymer layer (12). The anionic surfactant, by using the hydrophobicity thereof, can form a hydrophobic barrier layer in a solution to isolate a surface of the iron-based substrate (11) from a body fluid environment, thereby avoiding direct contact with an acidic environment resulting from degradation of the degradable polymer layer (12) at the initial and early stages of implantation, thus preventing severe local corrosion of the iron-based substrate (11).

11 Claims, 1 Drawing Sheet

IRON-BASED ABSORBABLE AND IMPLANTABLE MEDICAL DEVICE AND MANUFACTURING METHOD THEREOF

TECHNICAL FIELD

The present invention relates to the field of medical devices, and in particular, to an iron-based absorbable and implantable medical device and a manufacturing method thereof.

BACKGROUND ART

Many research efforts have reported using iron-based materials to manufacture a biological absorbable and implantable medical device. Compared with magnesium-based materials and degradable polymers, an implantable medical device is made of the iron-based alloy which has more ideal strength and slower absorption speed. For example, an iron-based alloy intraluminal scaffold can provide enough effective support during the healing stage of the lumen tissue (for example, the healing stage of vessel is about 3 months). However, there is a drawback of iron-based intraluminal scaffold that after the lumen tissue is repaired, the iron-based intraluminal scaffold corrodes slowly and does not completely corrode in the short-term. Therefore, the clinical degradation time requirement for an absorbable device cannot be satisfied, so the iron corrosion speed needs to be improved.

The prior art discloses that an iron-based substrate with degradable polyester coating on its surface can improve the corrosion speed of the iron-based alloy. The corrosion speed of iron-based material is demonstrated to significantly improve by accelerating its corrosion in a local subacidic environment near the implantation location of the device resulting from the degradation of a degradable polyester, which decreases the pH of local environment. Corrosion products of an iron-based material were obtained when the iron-based material corroded.

Whether the mass of the iron-based materials matches the mass of the degradable polyester coat affects the corrosion speed of the iron-based material and the final corrosion product morphology. For a given specification iron-based device, when the degradable polyester type and mass of the degradable polyester that is sufficient to completely corrode the iron-based substrate are determined, whether the degradation speed of the degradable polyester matches the corrosion speed of the iron-based alloy affects the early mechanical performance of the implantable device. For example, local corrosion may easily occur in the iron-based substrate at initial implantation (for example, after 1 to 7 days of implantation to a coronary artery) and during early periods (within one month after implantation). If the local corrosion occurs too quickly, a large amount of corrosion products accumulate. Therefore, endothelialization of the device is incomplete, and the risks of acute and sub-acute thrombosis are high. Some parts of the substrate may crack when corrosion is severe, and the device fails to provide effective support. Therefore, for an iron-based device including a degradable polyester, at present, a significant problem that needs to be addressed is to avoid local corrosion of the iron-based device at the initial and short-term periods after implantation so as to ensure safety and effectiveness of the iron-based device.

SUMMARY OF THE INVENTION

The objective of the present invention is to provide an iron-based absorbable and implantable medical device, and a manufacturing method thereof to avoid the local corrosion of the iron-based device at the initial and early periods after implantation. After the medical device is implanted into the body, during the early period, the corrosion of the iron-based substrate is relatively slow or does not occur, which can satisfy clinical mechanical performance requirements for devices during this early period.

A technical solution used by the present invention to solve the technical problem thereof is to provide an iron-based absorbable and implantable medical device, including a substrate and a degradable polymer layer, where the implantable medical device further includes an anionic surfactant layer, and the anionic surfactant layer is located between the substrate and the degradable polymer layer.

In the iron-based absorbable and implantable medical device according to an embodiment of the present invention, the anionic surfactant layer is connected to the substrate by chemical absorption.

In the iron-based absorbable and implantable medical device according to an embodiment of the present invention, anionic surfactant in the anionic surfactant layer includes a hydrophilic group and a hydrophobic chain, wherein the hydrophilic group is a polar hydrophilic group, and the hydrophobic chain is a non-polar hydrophobic chain.

In the iron-based absorbable and implantable medical device according to an embodiment of the present invention, the hydrophilic group is selected from at least one of carboxylic acid group, sulfate group, and sulfonate group.

In the iron-based absorbable and implantable medical device according to an embodiment of the present invention, the hydrophobic chain includes hydrocarbon chain, and the quantity of carbon atoms in the hydrocarbon chain is at least 8.

In the iron-based absorbable and implantable medical device according to an embodiment of the present invention, the anionic surfactant is selected from at least one of sodium dodecyl sulphate, sodium dodecyl sulfonate, and sodium dodecyl benzene sulfonate.

In the iron-based absorbable and implantable medical device according to an embodiment of the present invention, the anionic surfactant layer includes a single hydrophilic group layer or several hydrophilic group layers.

In the iron-based absorbable and implantable medical device according to an embodiment of the present invention, the iron-based absorbable and implantable medical device further includes an intermediate layer located between the substrate and the said anionic surfactant layer; the intermediate layer is a rough surface layer of iron-based substrate, iron oxide compound layer, or iron phosphate compound layer.

In the iron-based absorbable and implantable medical device according to an embodiment of the present invention, the degradable polymer layer is mixed with active drug ingredients, and the active drug includes anti-hyperplasia drug, anti-platelet drug, anti-thrombotic drug, an anti-inflammatory response drug, or a mixture of at least two of the said foregoing drugs.

In the iron-based absorbable and implantable medical device according to an embodiment of the present invention, the anti-hyperplasia drug comprises paclitaxel, rapamycin, and derivatives thereof; the anti-platelet drug includes cilostazol (Cilostazol); the anti-thrombotic drug includes heparin; and the anti-inflammatory drug includes dexamethasone.

The present invention further provides a manufacturing method of the iron-based absorbable and implantable medical device, including covering anionic surfactant layer on the surface of a substrate.

In the manufacturing method of the iron-based absorbable and implantable medical device according to an embodiment of the present invention, including the steps of covering the surface of the substrate with anionic surfactant layer, and soaking the substrate in anionic surfactant solution to form the anionic surfactant layer.

In the manufacturing method of the iron-based absorbable and implantable medical device according to an embodiment of the present invention, the soaking solution contains a positive electrode and a negative electrode, and direct current voltage is loaded between the positive electrode and the negative electrode.

In the manufacturing method of the iron-based absorbable and implantable medical device according to an embodiment of the present invention, the substrate is used as the positive electrode, or the substrate is electrically connected to the positive electrode, or the substrate is placed close to the positive electrode.

In the manufacturing method of the iron-based absorbable and implantable medical device according to an embodiment of the present invention, the manufacturing method includes performing surface modification on the substrate to form the intermediate layer before covering the anionic surfactant layer on the surface of the substrate.

In the manufacturing method of the iron-based absorbable and implantable medical device according to an embodiment of the present invention, the surface modification includes performing roughening processing, oxidation processing, or phosphating processing on the surface of the said substrate.

In the manufacturing method of the iron-based absorbable and implantable medical device according to an embodiment of the present invention, before covering the anionic surfactant layer on the surface of the said substrate, the manufacturing method includes cleaning the iron-based substrate.

An anionic surfactant layer is covered on the substrate of the medical device in the present invention. The anionic surfactant, by using the hydrophobicity thereof, can form a hydrophobic barrier layer in a solution to isolate a surface of the iron-based substrate from a body fluid environment, thereby avoiding direct contact with an acidic environment resulting from degradation of the degradable polymer layer at initial and early stages of implantation, thus preventing local corrosion of the iron-based substrate.

BRIEF DESCRIPTION OF THE DRAWINGS

The following further describes the present invention with reference to accompany drawings and embodiments. In the accompany drawings.

DETAILED DESCRIPTION OF THE INVENTION

The iron-based absorbable and implantable medical device provided by the present invention includes an intraluminal stent, a gynecological implant, an andrological implant, a respiratory implant, or an orthopedic implant. To more clearly understand the technical features, objectives, and effects of the present invention, an intraluminal stent is used as an example to describe specific embodiments of the present invention in detail with the accompany drawings.

Figure 1:
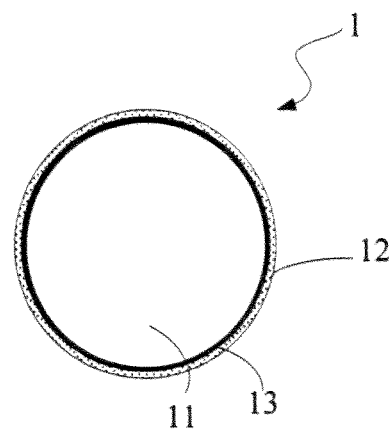
FIG. 1 is a schematic diagram of a cross-section of an absorbable intraluminal stent according to an embodiment of the present invention.

As shown in FIG. 1, an absorbable intraluminal stent 1 (hereinafter called the stent 1) includes an iron-based absorbable intraluminal stent substrate 11 (hereinafter called the substrate 11) and a degradable polymer layer 12 covering the substrate 11. The stent 1 may be a vessel stent such as a coronary stent or a peripheral stent, and has a radial compression state and a radial expansion state. The stent 1 in the radial compression state is mounted on a delivery device and is delivered to the location of a lesion in a lumen by the delivery device. After expansion, the stent 1 is expands to the radial expansion state by a balloon so as to attach to the lumen wall and be fixed in the lumen by means of the radial support force.

The degradable polymer layer 12 is used to load drugs and accelerate degradation of the substrate 11 by means of an acidic environment formed by its degradation products. The degradable polymer may be degradable polyester or degradable polyanhydride, which can generate carboxylic acid after degradation. The degradable polyester is selected from any one of polylactic acid, polyglycolic acid, polybutylene succinate, poly($\beta$-hydroxybutyrate), polycaprolactone, polyethylene glycol adipate, a polylactic acid-glycolic acid copolymer, or a poly hydroxybutyrate pentanoate copolymer; or selected from a physical blend of at least two of polylactic acid, polyglycolic acid, polybutylene succinate, poly($\beta$-hydroxybutyrate), polycaprolactone, polyethylene glycol adipate, a polylactic acid-glycolic acid copolymer, and a poly hydroxybutyrate pentanoate copolymer; or a copolymer formed by copolymerization of at least two monomers forming polylactic acid, polyglycolic acid, polybutylene succinate, poly($\beta$-hydroxybutyrate), polycaprolactone, polyethylene glycol adipate, the polylactic acid-glycolic acid copolymer, and the poly hydroxybutyrate pentanoate copolymer. The polyanhydride is selected from poly 1,3-bis (carboxyphenoxy)propane-sebacylic acid, poly erucic acid dimer-sebacylic acid, or poly fumaric acid-sebacylic acid. The degradable polyester is selected from any one of polylactic acid, polyglycolic acid, polybutylene succinate, poly ($\beta$-hydroxybutyrate), polycaprolactone, polyethylene glycol adipate, the polylactic acid-glycolic acid copolymer, or the poly hydroxybutyrate pentanoate copolymer. Alternatively, the degradable polymer includes a blend of the degradable polyester and the degradable polyanhydride, or a degradable copolymer formed by copolymerization of monomers of the degradable polyester or the degradable polyanhydride.

When the degradable polymer loads drugs, the degradable polymer layer may also be mixed with active drug ingredients, and the active drug may be anti-hyperplasia drug such as paclitaxel, rapamycin, and derivatives thereof. Alternatively, anti-platelet drug is selected from cilostazol (Cilostazol), anti-thrombotic drug such as heparin, anti-inflammatory drug such as dexamethasone, or mixture of at least two of these drugs.

The substrate 11 is formed by cutting an iron tube to preset patterns. The substrate 11 is made of an iron-based alloy. The iron-based alloy is selected from pure iron or alloy formed by doping at least one of C, N, O, S, P, Mn, Pd, Si, W, Ti, Co, Cr, Cu, Re in the pure iron. The content of all the impurity elements in the pure iron is less than or equal to 0.5 wt. %, and the content of all the alloy elements of the iron alloy is less than or equal to 3 wt. %. In one embodiment of the present invention, the carbon content in all the impurity elements of the pure iron may be less than or equal to 0.022%, or the carbon content in all the alloy elements of the iron alloy is less than or equal to ≤0.45 wt. %.

The absorbable intraluminal stent 1 further includes an anionic surfactant layer 13 located between the substrate 11 and the degradable polymer layer 12. The anionic surfactant in the anionic surfactant layer 13 includes hydrophilic group and hydrophobic chain, and the hydrophilic group is chemically absorbed to the iron-based substrate. The hydrophilic group is polar hydrophilic group such as carboxylic acid group, sulfate group, or sulfonate group. The hydrophobic chain is non-polar hydrophobic chain, including a hydrocarbon chain. The number of carbon atoms in the hydrocarbon chain is at least 8. The anionic surfactant may include single hydrophilic group and single hydrophobic chain. The anionic surfactant may also be anionic Gemini surfactant composed of dimer including the single hydrophilic group head and the single hydrophobic chain, or an oligomer including the single hydrophilic group head and the single hydrophobic chain. As an example, the anionic surfactant may be sodium dodecylsulphate, sodium dodecyl sulfonate, or sodium dodecyl benzene sulfonate.

The polar hydrophilic group of the anionic surfactant in the present invention can provide lone pair electrons, which generate chemical absorption by coordination reaction with ferric ions with empty 3D electron orbits. For chemical absorption, absorption molecules are absorbed on the surface of the medium by forming chemical bonds with surface atoms. The binding energy of the absorption greatly exceeds the binding energy of physical absorption through the van der Waals bond. Therefore, the anionic surfactant can be firmly absorbed on the surface of the iron-based substrate, and will not be separated. The non-polar hydrophobic chain of the anionic surfactant can form a hydrophobic barrier layer in solution to isolate the surface of the iron-based substrate from a body fluid environment, thereby avoiding direct contact with an acidic environment resulting from degradation of the degradable polymer layer at the initial and early stages after implantation, thereby preventing local corrosion of the iron-based substrate. In other words, in the present invention, as a corrosion inhibition layer, the anionic surfactant layer functions to prevent corrosion (or corrosion inhibition) of the iron-based substrate in the initial and early stages.

However, not all the biocompatible anionic surfactants can provide ferric ions with lone pair electrons for coordination to form chemical absorption. For example, stearate (including magnesium stearate and calcium stearate) that are commonly used in the field of implantable medical devices, such as magnesium stearate and calcium stearate, are insoluble in water; they cannot be ionized in water, and can only exist in the form of molecules. In addition, magnesium stearate and calcium stearate are generally soluble in organic solvents such as acetone, but organic solvents cannot provide hydrogen ions required for hydrolysis of magnesium stearate or calcium stearate. Therefore, magnesium stearate and calcium stearate are still dissolved in the form of molecules in these solvents. Oxygen atoms that can provide lone pair electrons are surrounded by magnesium/calcium atoms or carbon atoms, and oxygen atoms are shielded to provide lone pair electrons. If solvents that can provide hydrogen ions are provided, magnesium or calcium is replaced by hydrogen atoms in the solvents, so that oxygen atoms that can provide lone pair electrons can be exposed. However, the acidity of the solvents is greater than that of the water solution, which causes surface corrosion of the iron stent substrate, so as to cause other safety and effectiveness problems. Therefore, ideal samples cannot be manufactured.

During the process of using the anionic surfactant for anti-corrosion, because the anionic surfactant does not react with any acid or alkali, the anionic surfactant does not influence the acidic environment required for degradation of the stent, thereby ensuring normal degradation of the stent after the vascular repair period. Moreover, the hydrophobic chain of anionic surfactant was used to inhibit the corrosion. Because of the movement of molecules and molecular interaction, medium in the body can still slowly reach the surface of the stent through spaces between different hydrophobic chains, resulting in stent corrosion, and avoiding the non-corrosion or slowed corrosion of the iron-based substrate because of a thick corrosion inhibition layer or a very dense corrosion inhibition layer.

The anionic surfactant layer may include single hydrophilic group layer. That is, the surface of the iron-based substrate is only absorbed with single hydrophilic group layer. If the thickness of the anionic surfactant layer is characterized as the thickness of the hydrophilic group, the thickness of the anionic surfactant layer is about the size of the single hydrophilic group. The anionic surfactant layer may also include several hydrophilic groups, with the quantity being 2 to 9, and generally 2 to 3. At this time, the thickness of the anionic surfactant layer is about the sum of the sizes of the several hydrophilic groups. Regardless of single or several hydrophilic groups, the thickness of the anionic surfactant layer is in the nanometer level or smaller.

It is known that when a stent changes from the radial compression state to the radial expansion state, some areas of the stent have relatively large deformation, because the thickness of the anionic surfactant layer is in the nanometer level or smaller for the present invention. On one hand, the anionic surfactant layer does not increase the profile of the stent; on the other hand, the anionic surfactant layer does not crack due to its strong plastic deformation capability when the stent is radially expanded, thereby avoiding local corrosion of the iron-based substrate by the body fluid through cracks. Meanwhile, the radial support force of the stent is also not affected by the anionic surfactant layer.

Figure 2:
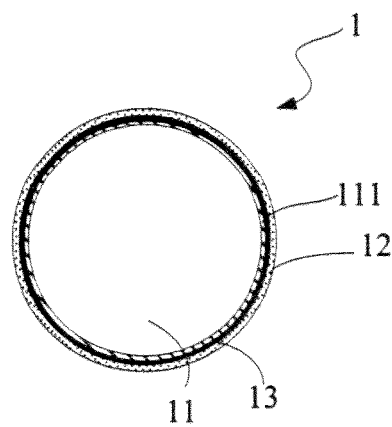
FIG. 2 is a schematic diagram of a cross-section illustrating an embodiment of a method of the absorbable intraluminal stent of FIG. 1.

As shown in FIG. 2, the substrate 11 may also include an intermediate layer 111 located between the substrate 11 and the anionic surfactant layer 13. The intermediate layer 111 may be a rough surface layer, iron oxide compound layer, or iron phosphate compound layer of the substrate 11. Compared with the original surface of the substrate 11, the surface of the intermediate layer 11 is much rougher, and can absorb more anionic surface active molecules or absorb anionic surfactant molecules easily. Moreover, the iron oxide compound and the iron phosphate compound layer inhibit corrosion, which can act together with the anionic surfactant layer 13 to further enhance the entire corrosion inhibition qualities of the stent.

The manufacturing method of the absorbable intraluminal stent includes manufacturing the above substrate and covering degradable polymer layer on the surface of the manufactured substrate. An appropriate method for covering the degradable polymer layer on the surface of the substrate was carried out by an ordinary skilled person in the art of implantable medical devices. The degradable polymer layer is used to load drugs and accelerate degradation of the substrate 11 by means of an acidic environment formed by its degradation products, such as the degradable polymer may generate carboxylic acid after degradation, and may be degradable polyester or degradable polyanhydride. The degradable polyester is selected from any one of polylactic acid, polyglycolic acid, polybutylene succinate, poly(β-hydroxybutyrate), polycaprolactone, polyethylene glycol adipate, a polylactic acid-glycolic acid copolymer, or a poly hydroxybutyrate pentanoate copolymer; or selected from a physical blend of at least two of polylactic acid, polyglycolic acid, polybutylene succinate, poly(β-hydroxybutyrate), polycaprolactone, polyethylene glycol adipate, a polylactic acid-glycolic acid copolymer, and a poly hydroxybutyrate pentanoate copolymer; or a copolymer formed by copolymerization of at least two of monomers forming polylactic acid, polyglycolic acid, polybutylene succinate, poly(β-hydroxybutyrate), polycaprolactone, polyethylene glycol adipate, the polylactic acid-glycolic acid copolymer, and the poly hydroxybutyrate pentanoate copolymer. The polyanhydride is selected from poly 1,3-bis(carboxyphenoxy)propane-sebacylic acid, poly erucic acid dimer-sebacylic acid, or poly fumaric acid-sebacylic acid. The degradable polyester is selected from any one of polylactic acid, polyglycolic acid, polybutylene succinate, poly(β-hydroxybutyrate), polycaprolactone, polyethylene glycol adipate, the polylactic acid-glycolic acid copolymer, or the poly hydroxybutyrate pentanoate copolymer. Alternatively, the degradable polymer includes a blend of the degradable polyester and the degradable polyanhydride, or a degradable copolymer formed by copolymerization for forming monomers of the degradable polyester and the degradable polyanhydride.

The degradable polymer is also used to load drugs, the degradable polymer layer may also be mixed with active drug ingredients, and the active drug may be anti-hyperplasia drug such as paclitaxel, rapamycin, and derivatives thereof. Alternatively, antiplatelet drug is selected from cilostazol (Cilostazol), antithrombotic drug such as heparin, anti-inflammatory response drug such as dexamethasone, or mixture of the at least two foregoing drugs.

The method for manufacturing the absorbable intraluminal stent includes covering the anionic surfactant layer on the surface of the iron-based substrate, for example, submersing the iron-based substrate into anionic surfactant soaking solution (which can be called the soaking solution) to form the anionic surfactant layer. The soaking solution may be anionic surfactant solution with concentration ranges from 0.003 mol/L to 0.1 mol/L, the soaking time is generally 1 to 2 hours, and the soaking temperature is 20 to 40° C.

The anionic surfactant in the anionic surfactant solution includes a hydrophilic group and hydrophobic chain, and the hydrophilic group is connected to the iron-based substrate by chemical absorption. The hydrophilic group is polar hydrophilic group such as carboxylic acid group, sulfate group, or sulfonate group. The hydrophobic chain is nonpolar hydrophobic chain, including hydrocarbon chain. A quantity of carbon atoms in the hydrocarbon chain is at least 8. The anionic surfactant may include single hydrophilic group and single hydrophobic chain. The anionic surfactant may also be anionic Gemini surfactant composed of dimer including the single hydrophilic group and the single hydrophobic chain, or an oligomer including the single hydrophilic group and the single hydrophobic chain. Specifically, the anionic surfactant may be sodium dodecyl sulphate, sodium dodecyl sulfonate, or sodium dodecyl benzene sulfonate.

If the iron-based substrate is directly submersed into the soaking solution for reaction, the concentration of the soaking solution is 0.003 mol/L-0.1 mol/L, the soaking reaction time is generally 1 to 2 hours, and the soaking temperature is 20 to 40° C. The anionic surfactant automatically absorbs to the surface of the iron-based substrate during the soaking reaction.

In an automatic absorption process, if the concentration of the anionic surfactant is relatively low, for example, the concentration of the anionic surfactant is lower than a critical micelle concentration of the anionic surfactant, the automatic absorption process is relatively slow. At this time, an electric field can be added to the soaking reaction, so as to reduce ion collision in the soaking solution by using the electric field force, which promotes the ions to directionally move and improves the moving speed of ions to accelerate the absorption of anionic surfactant. Specifically, a positive electrode and a negative electrode may be added to the soaking solution. A direct current voltage is loaded between the positive electrode and the negative electrode, and the direct current voltage ranges from 5 to 20V. The iron-based substrate can be directly used as the positive electrode, or can be electrically connected to the positive electrode. At this time, the concentration of the soaking solution is 0.003 mol/L-0.03 mol/L, the soaking reaction time is generally 3 to 5 minutes, and the soaking temperature is 20 to 40° C. The iron-based substrate can be placed near the positive electrode, but it is not electrically connected to the positive electrode. At this time, the concentration of the soaking solution is 0.003 mol/L-0.03 mol/L, the soaking reaction time is generally 10 to 30 minutes, and the soaking temperature is 20 to 40° C.

In the manufacturing method of the absorbable intraluminal stent, before covering the anionic surfactant layer on the surface of the iron-based substrate, surface modification can be performed on the surface of the iron-based substrate to form the intermediate layer 111. For example, the surface modification may be performed on the surface of the iron-based substrate by a roughening processing to form a rough surface layer, and the roughening process may roughen an original surface of the iron-based substrate. The surface modification may also be oxidization processing on the surface of the iron-based substrate to form the intermediate layer lll of the iron oxide compound. The oxidization processing may be by heating oxidization, soaking reaction oxidization, or chemical vapor deposition oxidization. The surface modification may also be phosphating processing on the surface of the iron-based substrate to form a phosphate compound layer. The phosphate processing may be performed by placing the iron-based substrate in a phosphate solution for soaking reaction.

In the manufacturing method of the absorbable intraluminal stent, before covering the anionic surfactant layer on the surface of the iron-based substrate, the iron-based substrate is cleaned, for example, the iron-based substrate is placed into a cleaning solution for ultrasonic cleaning to ensure that the surface finish of the iron-based substrate can facilitate absorption of the anionic surfactant molecules on the surface of the iron-based substrate.

Embodiment 1

During a process of manufacturing the absorbable intraluminal stent, the iron-based substrate is placed in anionic surfactant soaking solution. The soaking solution is an aqueous solution of sodium dodecyl sulphate, the concentration is 0.05 mol/L, the soaking temperature is 20 to 40° C., and the soaking reaction time is 1 to 2 hours. After the soaking, the obtained substrate is taken out and cleaned by alcohol, and dried under 40 to 60° C.

A contact angle test is performed on the obtained substrate and an empty sample at the same time. A JY-82 video contact angle machine is used to test contact angles of the substrate and the iron-based substrate by angle measurement, so as to evaluate hydrophilicity of the respective substrates. Certainly, any appropriate method for angle measurement can be carried out by an ordinary skilled person in implantable medical devices field. For example, height measurement can also be selected for testing. Here, the contact angle of the substrate measured by angle measurement is 850, and the contact angle of the iron-based substrate is 33°.

In-vitro simulation corrosion testing of the substrate with surfactant and the iron-based substrate without surfactant (which is hereinafter called an empty sample) are performed at the same time. The respective substrates are placed in a corrosion solution for corrosion. The corrosion solution is physiological saline. Then the corrosion solution is sealed, and is placed in a shaking bath under 37° C. for corrosion for an hour. Here, the corrosion solution is ordinary physiological saline, and no special acidizing processing is performed to simulate an acidic environment formed by degradation products of the polymer. On one hand, in the initial or early stages after implantation of the stent, the degradation products of the polymer only form acidic environment in local areas of the stent, and do not obviously affect the whole pH value of the body fluid environment surrounding the stent. On the other hand, the anionic surfactant in the present invention provides anti-corrosion or corrosion inhibition through hydrophobicity. Regardless of whether ordinary physiological saline or physiological saline with acidizing processing is performed, the anti-corrosion or corrosion inhibition principles are the same, as both saline is blocked outside the surfactant. The physiological saline with acidizing processing contains a small amount of hydrogen ions. However, because the hydrophobic chain repels water molecules, hydrogen ions cannot keep the ion species from reaching the surface of the iron-based substrate, and cannot independently corrode the iron-based substrate. In conclusion, in the in-vitro simulation corrosion experiment, ordinary physiological saline used as corrosion solution can effectively simulate the environment of the implanted stent.

After corrosion, the stent is cleaned and weighed, and the corrosion weight loss result is used to characterize the corrosion speed. The unit of corrosion weight loss is mm/y, and the calculation formula is $(10<-2>\cdot \Delta M)/(\rho \cdot S \cdot t)$. $\Delta M$ uses g as a unit to represent mass loss before and after the corrosion; the corrosion time t uses year (y) as a unit for calculation; superficial area S of an object uses cm<2> as a unit for calculation, and $\rho$ uses g/cm<3> as a unit for calculation, for example, if the material is pure iron, $\rho=7.8$ g/cm<3>.

After soaking corrosion for one hour, samples are observed under a three-dimensional stereomicroscope. The substrate with the surfactant does not corrode, and the corrosion solution is macroscopically clear. The empty sample has obvious corrosion points, and the corrosion solution is macroscopically a little light yellow turbid. A calculated corrosion speed of the substrate is 0.0409 mm/y, and under the same condition, the corrosion speed of the iron-based substrate is 0.0613 mm/y.

It can be seem from the foregoing results that covering the anionic surfactant layer on the surface of the iron-based substrate can decrease the corrosion speed, so as to avoid or delay the local corrosion at the initial and early stages after stent implantation, and meanwhile, weaken the hydrophilicity. Compared with the empty sample, the contact angle of the absorbable intraluminal stent of this embodiment increases from 33° to 85°; that is, the corresponding hydrophobicity improved and the corrosion inhibition performance is enhanced.

Embodiment 2

During a process of manufacturing the absorbable intraluminal stent, ultrasonic cleaning is first performed on the iron-based substrate. The ultrasonic cleaning solution is dilute hydrochloric acid solution. A known concentration can be used by an ordinary skilled person in the field of implantable medical devices, and the ultrasonic cleaning time is 1 to 3 minutes. Then ultrasonic cleaning is respectively performed for 1 minute by sequentially using 5% of sodium hydroxide solution, primary purified water, and alcohol. After the ultrasonic cleaning, an anionic surfactant layer is covered on the surface of the metal substrate by soaking reaction. At this time, the soaking solution is aqueous solution of sodium dodecyl sulfonate, the concentration is 0.05 mol/L, and the soaking time is 1 to 2 hours. After the reaction, the obtained substrate is taken out and cleaned by alcohol, and dried under 40 to 60° C. In this embodiment, before covering the anionic surfactant, ultrasonic cleaning is first performed on the iron-based substrate so as to ensure the finished degree of the stent surface. Meanwhile, on the premise that the mass of the iron-based substrate has no obvious change, the coarse degree of a molecule level of the surface of the iron-based substrate can be improved, and more iron atoms are exposed so as to absorb more anionic surfactant molecules and provide a better corrosion inhibition effect.

The same methods described in embodiment 1 are used to perform in-vitro simulation corrosion testing and contact angle testing on the obtained substrate and the iron-based substrate. In the in-vitro simulation corrosion test, under a three-dimensional stereomicroscope, it is observed that the substrate does not corrode, and the soaking solution is macroscopically clear. The empty sample has obvious corrosion points, and the soaking solution is macroscopically a little light yellow turbid. A calculated corrosion speed of the substrate is 0.0385 mm/y, and under the same condition, corrosion speed of the iron-based substrate is 0.0613 mm/y. The measured contact angle of the substrate is 93°, and the contact angle of the iron-based substrate is 33°. The test result indicates that, compared with the iron-based substrate, the corrosion speed of the substrate of the present invention obviously decreases, and the hydrophobicity obviously enhanced. Therefore, a relatively good corrosion inhibition effect can be obtained.

Embodiment 3

During a process of manufacturing a substrate, thermal treatment is first performed on the iron-based substrate for 30 seconds to 3 minutes in an air atmosphere with temperature ranges from 300 to 350° C. and a well-distributed iron oxide compound intermediate layer is formed on the surface of the iron-based substrate. Usually, the thickness of the intermediate layer is in nanometer level. Subsequently, an anionic surfactant layer is covered on the intermediate layer by a soaking reaction method. The soaking solution is aqueous solution of sodium dodecyl sulfonate, the concentration is 0.05 mol/L, and the soaking reaction time is 1 to 2 hours. After the soaking reaction, the obtained substrate is taken out and cleaned by alcohol, and dried under 40 to 60°. In this embodiment, the iron oxide compound intermediate layer not only enhances the degree of coarseness, but also enables the intermediate layer to absorb anionic surfactant molecules easily. Meanwhile, the iron oxide compound intermediate layer itself provides a corrosion inhibition effect, and can have a slow release effect with the anionic surfactant layer.

The same methods described in embodiment 1 are used to perform in-vitro simulation corrosion testing and contact angle testing on the obtained substrate and the iron-based substrate. In the in-vitro simulation corrosion test, under three-dimensional stereomicroscope, it is observed that the substrate does not corrode, and the soaking solution is macroscopically clear. The empty sample has obvious corrosion points, and the soaking solution is macroscopically a little light yellow turbid. The measured contact angle of the substrate is 100°, and the contact angle of the iron-based substrate is 33°. The test result indicates that, compared with the iron-based substrate, the corrosion inhibition effect of the substrate of the present invention is obvious.

Embodiment 4

During a process of manufacturing the substrate, phosphate processing is first performed on the iron-based substrate, and the composition of the phosphate solution is: oxalic acid 20 g/L, sodium oxalate 4 g/L, sodium dihydrogen phosphate 10 g/L, and sodium chlorate 12 g/L. The phosphate processing temperature is 20 to 25° C. and the time is 5 minutes. The composition of the phosphate solution set forth herein is not limiting and is intended to be an example only. Any appropriate phosphate solution can be used by an ordinary skilled person in the field of implantable medical devices. An iron phosphate compound intermediate layer is formed on the surface of the iron-based substrate by phosphate processing. Usually, the thickness of the intermediate layer is in the nanometer level.

Subsequently, anionic surfactant layer is covered on the intermediate layer by using a soaking reaction method. The soaking solution is aqueous solution of sodium dodecyl benzene sulfonate, the concentration is 0.05 mol/L, and the soaking reaction time is 1 to 2 hours. After the soaking reaction, the obtained substrate is taken out and cleaned by alcohol, and dried under 40 to 60°. In this embodiment, the iron phosphate compound intermediate layer not only enhances the degree of coarseness, but also enables the intermediate layer to easily absorb anionic surfactant molecules. Meanwhile, the iron phosphate compound intermediate layer provides a corrosion inhibition effect, and can have a slow release effect with the anionic surfactant layer.

The same methods described in embodiment 1 are used to perform in-vitro simulation corrosion testing and contact angle testing on the obtained substrate and the iron-based substrate. In the in-vitro simulation corrosion test, under a three-dimensional stereomicroscope, it is observed that the substrate does not corrode, and the soaking solution is macroscopically clear. The iron-based substrate has obvious corrosion points, and the soaking solution is macroscopically a little light yellow turbid. The measured contact angle of the substrate is 98°, and the contact angle of the iron-based substrate is 33°. The test result indicates that, compared with the iron-based substrate, the corrosion inhibition effect of the substrate of the present invention is obvious.

Embodiment 5

Figure 3:
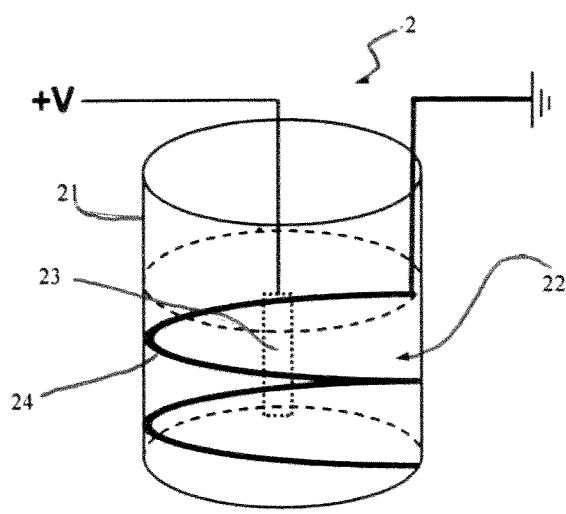
FIG. 3 is schematic diagram of a soaking reaction apparatus according to an embodiment of the present invention.

As shown in FIG. 3, during a process of manufacturing the substrate, the iron-based substrate is placed in a soaking reaction apparatus 2 for soaking reaction. The soaking reaction apparatus 2 includes a container 21, and soaking solution 22 in the container 21. Meanwhile, the soaking solution 22 has a positive electrode 23 and a negative electrode 24 in it, and direct current voltage is loaded between the positive electrode 23 and the negative electrode 24. In the soaking reaction of this embodiment, the soaking solution 22 is aqueous solution of sodium dodecyl sulfonate. The concentration is 0.013 mol/L, and the temperature of the soaking solution 22 is 20 to 40° C. The metal substrate is electrically connected to a positive electrode of a power source and is used as a positive electrode 23 directly. The negative electrode 24 is lead electrode, a loaded voltage is 10V, and the soaking reaction time is 5 minutes. After the soaking reaction ends, the obtained substrate is taken out and cleaned by alcohol, and dried under 40 to 60°.

The same methods described in embodiment 1 are used to perform in-vitro simulation corrosion testing and contact angle testing on the obtained substrate and the iron-based substrate. In the in-vitro simulation corrosion test, under a three-dimensional stereomicroscope, it is observed that the substrate does not corrode, and the soaking solution is macroscopically clear. The iron-based substrate has obvious corrosion points, and the soaking solution is macroscopically a little light yellow turbid. The calculated corrosion speed of the substrate is 0.0436 mm/y, and under the same condition, the corrosion speed of the iron-based substrate is 0.0613 mm/y. The measured contact angle of the substrate is 800, and the contact angle of the iron-based substrate is 33°. The test result indicates that, compared with the iron-based substrate, the corrosion speed of the substrate of the present invention obviously decreases, and the hydrophobicity is obviously enhanced. Therefore, a relatively good corrosion inhibition effect can be obtained.

In this embodiment, the electric field can be added to the soaking reaction, so as to enable the charged ions in the solution to directionally move, to reduce collision between ions, to enable a greater number of anionic surfactant molecules to arrive at the vicinity of the iron-based substrate at faster speeds, and to be more easily absorbed into the iron-based substrate, thereby improving the absorption efficiency and reducing the soaking reaction time.

Embodiment 6

The difference between embodiment 5 and embodiment 6 is that ultrasonic cleaning is performed on the iron-based substrate before the soaking reaction. The ultrasonic cleaning solution is dilute hydrochloric acid solution. A known concentration can be used by an ordinary skilled person in the field of implantable medical devices, and the ultrasonic cleaning time is 1 to 3 minutes. Then ultrasonic cleaning is performed for 1 minute by using 5% of a sodium hydroxide solution, primary purified water, and alcohol, sequentially.

The same methods described in embodiment 1 are used to perform in-vitro simulation corrosion testing and contact angle testing on the obtained substrate and the iron-based substrate. In the in-vitro simulation corrosion test, under a three-dimensional stereomicroscope, it is observed that the substrate does not corrode, and the soaking solution is macroscopically clear. The iron-based substrate has obvious corrosion points, and the soaking solution is macroscopically a little light yellow turbid. The calculated corrosion speed of the substrate is 0.0428 mm/y, and under the same condition, a corrosion speed of the iron-based substrate is 0.0613 mm/y. The measured contact angle of the substrate is 810, and the contact angle of the iron-based substrate is 33°. The test result indicates that, compared with the iron-based substrate, the corrosion speed of the substrate of the present invention obviously decreases, and the hydrophobicity is obviously enhanced. Therefore, a relatively good corrosion inhibition effect can be obtained.

Embodiment 7

The difference between embodiment 5 and embodiment 7 is that the positive electrode and the negative electrode are two parallel stainless steel plate plates. The area of the electrode plate is equivalent to that of the soaking solution, and covers the whole soaking solution as much as possible. The distance between the electrode plates is about 5 cm. The iron-based substrate is placed near the positive electrode. Other soaking reaction parameters are the same as embodiment 5, except the soaking reaction time is adjusted to 10 to 30 minutes.

The same methods described in embodiment 1 are used to perform in-vitro simulation corrosion testing and contact angle testing on the obtained substrate and the iron-based substrate. In the in-vitro simulation corrosion test, under a three-dimensional stereomicroscope, it is observed that the substrate does not corrode, and the soaking solution is macroscopically clear. The iron-based substrate has obvious corrosion points, and the soaking solution is macroscopically a little light yellow turbid. The calculated corrosion speed of the substrate is 0.0396 mm/y, and under a same condition, the corrosion speed of the iron-based substrate is 0.0613 mm/y. The measured contact angle of the substrate is 87°, and the contact angle of the iron-based substrate is 33°. The test result indicates that, compared with the iron-based substrate, the corrosion speed of the substrate of the present invention obviously decreases, and the hydrophobicity is obviously enhanced. Therefore, a relatively good corrosion inhibition effect can be obtained.

In this embodiment, because the area of the electrode plate is compared with the size of the soaking solution, the greatest uniform electric field was obtained to cover the whole soaking solution, so as to enable the anionic surfactant on the iron-based substrate to absorb evenly.

Embodiment 8

The difference between embodiment 7 and embodiment 8 is that thermal treatment is performed on the iron-based substrate for 30 seconds to 3 minutes in an air atmosphere with a temperature of 300 to 350° C. before the soaking reaction, and a well-distributed iron oxide compound intermediate layer is formed on the surface of the iron-based substrate. The thickness of the intermediate layer is usually in the nanometer level.

The same methods described in embodiment 1 are used to perform in-vitro simulation corrosion testing and contact angle testing on the obtained substrate and the iron-based substrate. In the in-vitro simulation corrosion test, under a three-dimensional stereomicroscope, it is observed that the substrate does not corrode, and the soaking solution is macroscopically clear. The iron-based substrate has obvious corrosion points, and the soaking solution is macroscopically a little light yellow turbid. The measured contact angle of the substrate is 99°, and the contact angle of the iron-based substrate is 33°. The test result indicates that, compared with the iron-based substrate, the corrosion inhibition effect of the substrate of the present invention is obvious.

For the intraluminal stent of the present invention, the anionic surfactant layer is covered on a surface of iron-based substrate. The anionic surfactant layer is firmly connected to the iron-based substrate through chemical absorption. Meanwhile, the anionic surfactant, by using the hydrophobicity thereof, can isolate the iron-based substrate from a body fluid environment, thereby preventing local corrosion of the iron-based substrate in the initial and early stages after implantation. In addition, the anionic surfactant does not react with any acid or alkali, and the anionic surfactant does not consume the acidic environment required for degradation of the stent, thereby ensuring normal degradation of the stent after the vascular repair period.

The invention claimed is:

1. An iron-based absorbable and implantable medical device, comprising an iron-based substrate and a degradable polymer layer, wherein the implantable medical device further comprises an anionic surfactant layer located between the substrate and the degradable polymer layer; wherein the iron-based absorbable and implantable medical device further comprises an intermediate layer located between the substrate and the anionic surfactant layer; wherein the intermediate layer is a rough surface of the iron-based substrate, an iron oxide compound layer, or an iron phosphate compound layer; and wherein the anionic surfactant layer is absorbed to the iron present in the substrate and/or the intermediate layer.

2. The iron-based absorbable and implantable medical device according to claim 1, wherein the anionic surfactant present in the anionic surfactant layer is absorbed by the substrate by chemical adsorption.

3. The iron-based absorbable and implantable medical device according to claim 1, wherein the anionic surfactant in the anionic surfactant layer comprises a hydrophilic group and hydrophobic chain, wherein the hydrophilic group is a polar hydrophilic group, and the hydrophobic chain is a non-polar hydrophobic chain.

4. The iron-based absorbable and implantable medical device according to claim 3, wherein the hydrophilic group is selected from at least one of carboxylic acid group, sulfate group or sulfonate group.

5. The iron-based absorbable and implantable medical device according to claim 3, wherein the hydrophobic chain comprises a hydrocarbon chain, the hydrocarbon chain comprising at least 8 carbon atoms.

6. The iron-based absorbable and implantable medical device according to claim 1, wherein the anionic surfactant is selected from at least one of sodium dodecyl sulphate, sodium dodecyl sulfonate, or sodium dodecyl benzene sulfonate.

7. The iron-based absorbable and implantable medical device according to claim 3, wherein the anionic surfactant layer comprises a single hydrophilic group layer or several hydrophilic group layers.

8. The iron-based absorbable and implantable medical device according to claim 1, wherein the anionic surfactant present in the anionic surfactant layer is absorbed to the iron present in the intermediate layer.

9. The iron-based absorbable and implantable medical device according to claim 1, wherein the degradable polymer layer is mixed with an active drug, and the active drug comprises anti-hyperplasia drug, antiplatelet drug, anti-thrombotic drug, anti-inflammatory response drug, or a mixture of at least two of the drugs.

10. The iron-based absorbable and implantable medical device according to claim 9, wherein the anti-hyperplasia drug comprises paclitaxel, and rapamycin; the anti-platelet drug comprises cilostazol; the anti-thrombotic drug comprises heparin; and the anti-inflammatory drug comprises dexamethasone.

11. The iron-based absorbable and implantable medical device according to claim 1, wherein the anionic surfactant present in the anionic surfactant layer is absorbed to the iron present in the substrate.

* * * * *